(12) United States Patent
Zardi

(10) Patent No.: US 7,091,379 B2
(45) Date of Patent: Aug. 15, 2006

(54) PROCESS AND PLANT FOR THE PRODUCTION OF UREA

(75) Inventor: Federico Zardi, Breganzona (CH)

(73) Assignee: Urea Casale S.A. (CH)

( * ) Notice: Subject to any disclaimer, the term of this patent is extended or adjusted under 35 U.S.C. 154(b) by 72 days.

(21) Appl. No.: 10/513,189

(22) PCT Filed: Jan. 15, 2004

(86) PCT No.: PCT/EP2004/000234

§ 371 (c)(1),
(2), (4) Date: Nov. 1, 2004

(87) PCT Pub. No.: WO2004/074217

PCT Pub. Date: Sep. 2, 2004

(65) Prior Publication Data

US 2005/0256339 A1    Nov. 17, 2005

(30) Foreign Application Priority Data

Feb. 21, 2003    (EP) .................................. 03003878

(51) Int. Cl.
*C07C 273/04*    (2006.01)
*B01J 8/04*    (2006.01)

(52) U.S. Cl. ............................ 564/67; 564/70; 564/71; 564/72; 422/188

(58) Field of Classification Search .................. 564/67, 564/70, 71, 72; 422/188
See application file for complete search history.

(56) References Cited

U.S. PATENT DOCUMENTS 6,680,407 B1 * 1/2004 Mennen ....................... 564/72
2001/0041813 A1    11/2001 Jonckers et al.

* cited by examiner

*Primary Examiner*—Peter O'Sullivan
(74) *Attorney, Agent, or Firm*—Akerman Senterfitt

(57) ABSTRACT

A process for urea production comprises the steps of:—performing a reaction between ammonia and carbon dioxide in a reaction space to obtain a reaction mixture comprising urea, carbamate and free ammonia in aqueous solution,—subjecting said mixture to a stripping treatment with carbon dioxide feed as a stripping agent to obtain a first flow comprising ammonia and carbon dioxide in vapor phase and a flow comprising urea and residual carbamate in aqueous solution,—feeding said flow comprising urea and residual carbamate in aqueoue solution to a urea recovery section,—separating in said recovery section said residual carbamate from the urea to obtain a first flow of carbamate in aqueous solution.

9 Claims, 1 Drawing Sheet

PROCESS AND PLANT FOR THE PRODUCTION OF UREA

TECHNICAL FIELD

In its most general aspect the present invention relates to a process for urea production.

Specifically, the present invention relates to a process for urea production of the type comprising the steps of:
- performing a reaction between ammonia and carbon dioxide in a reaction space to obtain a reaction mixture comprising urea, carbamate and free ammonia in aqueous solution,
- subjecting said mixture to a stripping treatment with carbon dioxide feed as a stripping agent to obtain a first flow comprising ammonia and carbon dioxide in vapor phase and a flow comprising urea and residual carbamate in aqueous solution,
- feeding said flow comprising urea and residual carbamate in aqueous solution to a urea recovery section,
- separating in said recovery section said residual carbamate from the urea to obtain a first flow of carbamate in aqueous solution.

The present invention also relates to a plant for carrying out the above mentioned process.

PRIOR ART

It is well known to produce urea by a process as specified above which is carried out in a urea plant based on the so called "carbon dioxide stripping technology".

Such a plant is characterized by a substantially isobaric synthesis loop comprising as main components a synthesis reactor or reaction space, a stripper and a carbamate condenser.

According to the stripping technology, in the isobaric synthesis loop the majority of the unconverted ammonium carbamate is decomposed and the majority of the excess ammonia is removed at pressures nearly the same as the pressure in the synthesis reactor.

This decomposition and removal occurs in the stripper installed downstream of the reaction space. Although thermal stripping alone may be used, more typically, the reaction mixture comprising urea, carbamate and free ammonia in aqueous solution is fed into the stripper and a stripping gas, generally carbon dioxide, is also used to decompose the ammonium carbamate and remove the majority of the carbon dioxide and ammonia from the solution.

The gas stream coming from the stripper comprises mainly ammonia and carbon dioxide in vapor phase (first flow) and is typically fed into the carbamate condenser operating at or near the synthesis pressure.

This stream is typically subjected to a substantially total condensation to produce an ammonium carbamate solution that can be fed back into the synthesis reactor.

A process for urea production of this type is disclosed for example in WO 00/00466 in which the gas stream coming from the stripper is totally condensed in a submerged carbamate condenser and an ejector with liquid ammonia as driving fluid is used for recycling to the reactor the carbamate aqueous solution leaving the carbamate condenser.

However, this process suffers the disadvantage that a substantial portion of the carbon dioxide feed need to be sent directly to the reactor to secure the reactor thermal balance.

This significantly reduces the stripping efficiency leaving higher residual content of unreacted ammonia and carbon dioxide in the stripped urea solution to be processed with high investment and operating costs in the units of the urea recovery section downstream the isobaric synthesis loop.

DISCLOSURE OF INVENTION

The technical problem underlying the present invention is that of providing a process for urea production which achieve high conversion yield and, at the same time, would be technically simple to implement and would involve low investment, maintenance and operating costs.

In accordance with the present invention, this problem is solved by a process of the above mentioned type, which is characterized in that it comprises the additional steps of:
- subjecting a first portion of said first flow comprising ammonia and carbon dioxide in vapor phase to a substantially total condensation to obtain a second flow of carbamate in aqueous solution,
- recycling said second flow of carbamate in aqueous solution to said reaction space,
- recycling a second portion of said first flow comprising ammonia and carbon dioxide in vapor phase to said reaction space,
- subjecting at least part of said first flow of carbamate in aqueous solution obtained in said urea recovery section to a treatment of partial decomposition to obtain a second flow comprising ammonia and carbon dioxide in vapor phase and a flow comprising residual carbamate in aqueous solution,
- recycling said second flow comprising ammonia and carbon dioxide in vapor phase to said reaction space, or
- recycling said second flow comprising ammonia and carbon dioxide in vapor phase to said first portion of said first flow comprising ammonia and carbon dioxide in vapor phase and subjecting them to a substantially total condensation to obtain said second flow of carbamate in aqueous solution, or
- recycling said second flow comprising ammonia and carbon dioxide in vapor phase to said first flow comprising ammonia and carbon dioxide in vapor phase and subjecting a first portion thereof to a substantially total condensation to obtain said second flow of carbamate in aqueous solution and recycling a second portion thereof to said reaction space.

In order to obtain almost water free vapors and easy recycle to reactor of the same, said at least part of the first flow of carbamate in aqueous solution is preferably subjected to a treatment of partial decomposition at a pressure substantially corresponding to the pressure in the reaction space.

The process of the present invention comprises also the step of feeding the flow comprising residual carbamate in aqueous solution resulting from the treatment of partial decomposition of at least part of the first flow of carbamate in aqueous solution to said urea recovery section.

According to the present invention, preferably at least 60% of the first flow of carbamate in aqueous solution leaving the urea recovery section, most preferably at least 80% thereof, is advantageously subjected to a treatment of partial decomposition separating unreacted ammonia and carbon dioxide from a solution rich in water comprising residual carbamate.

According to the present invention, the heat balance in the reaction space is advantageously secured by the portion of first flow (and possibly by the second flow or a portion thereof comprising ammonia and carbon dioxide in vapor phase fed thereto.

At the same time, all carbon dioxide feed is advantageously used as stripping agent in the stripping treatment of the reaction mixture with consequent maximum stripping efficiency.

By operating in this manner, it is possible to obtain a high conversion yield in the reaction space since, by virtue of the high efficiency of the stripping treatment of the reaction mixture, a high recover of unreacted substances within the isobaric synthesis loop is obtained.

Moreover, the reduced amount of unreacted substances still present in the urea flow fed to the recovery section permits to reduce the load of such unit thus obtaining a debottlenecking of the plant to full advantage of the overall production capacity, which may be therefore optimally increased, and to the investment and operating costs that are consequently decreased with respect to the prior art.

According to another aspect of the present invention, the technical problem set forth above is solved by a plant designed to implement the urea production process of the invention. This plant comprises:

- a urea synthesis reactor for performing a reaction between ammonia and carbon dioxide obtaining a reaction mixture comprising urea, carbamate and free ammonia in aqueous solution,
- a first thermal stripping unit with also carbon dioxide as stripping agent for subjecting said reaction mixture to a treatment of partial decomposition of the carbamate and partial separation of the free ammonia in aqueous solution present in said mixture obtaining a first flow comprising ammonia and carbon dioxide in vapor phase and a flow comprising urea and residual carbamate in aqueous solution,
- a urea recovery section for separating urea from said flow comprising urea and residual carbamate in aqueous solution leaving the first stripping unit, obtaining a first flow of carbamate in aqueous solution, which is characterized in that it further comprises:

- means for substantially totally condensing a first portion of said first flow comprising ammonia and carbon dioxide in vapor phase obtaining a second flow of carbamate in aqueous solution,
- means for recycling said second flow of carbamate in aqueous solution to said urea synthesis reactor,
- means for recycling a second portion of said first flow comprising ammonia and carbon dioxide in vapor phase to said urea synthesis reactor,
- a second stripping unit for subjecting at least part of said first flow of carbamate in aqueous solution to a treatment of partial decomposition obtaining a second flow comprising ammonia and carbon dioxide in vapor phase,
- means for recycling said second flow comprising ammonia and carbon dioxide in vapor phase to said urea synthesis reactor, or
- means for recycling said second flow comprising ammonia and carbon dioxide in vapor phase to said condensing means, or
- means for recycling a first portion of said second flow comprising ammonia and carbon dioxide in vapor phase to said condensing means and a second portion of said second flow comprising ammonia and carbon dioxide in vapor phase to said urea synthesis reactor.

Preferably, said means for totally condensing the gaseous flow leaving the first stripping unit, and possibly the second stripping unit, comprise a vertical carbamate condensation unit of the "submerged type", i.e. an apparatus wherein the liquid phase fills (submerges) a tube bundle and wherein the condensation of the gaseous phase occurs by passing through such liquid phase.

In this way, an effective mixing of the gaseous phase in the liquid phase is achieved resulting in a high efficiency of the condensation and therefore in an equipment of a small size.

According to an aspect of the present invention, the above plant further comprises means for feeding a first portion of liquid ammonia feed in said reactor for urea synthesis and means for feeding a second portion of liquid ammonia feed to said condensing means.

Preferably, the amount of liquid ammonia to be sent to the reactor (first portion) is more than the amount of liquid ammonia to be sent to the condensing means (second portion).

The feed of a second portion of ammonia in the carbamate condensation unit significantly promotes the total condensation of the vapors coming from the stripping unit(s).

According to another aspect of the present invention, the above plant further comprises:

- means for preheating said at least part of the first flow of carbamate in aqueous solution to be sent to the second stripping unit, and
- means for preheating said first portion of liquid ammonia feed to be sent to the urea synthesis reactor and/or said second portion of liquid ammonia feed to be sent to the condensing means.

Advantageously, the above preheating steps are achieved using the heat removed in the condensing means (i.e. the carbainate condensation unit) to secure minimum energy consumption.

According to the present invention, the means for feeding the first portion of liquid ammonia feed to the reactor and the means for recycling the second flow of carbamate in aqueous solution to the reactor comprise:

- an ejector,
- means for feeding said second flow of carbamate in aqueous solution to the ejector,
- means for feeding said first portion of liquid ammonia feed to the ejector, and
- means for sending said second flow of carbamate in aqueous solution together with said first portion of liquid ammonia feed from the ejector to the urea synthesis reactor.

The above ejector advantageously uses the first portion of liquid ammonia feed as driving fluid.

According to a preferred embodiment of the present invention, the second stripping unit is a thermal stripping unit and the plant further comprises means for feeding all carbon dioxide feed to said first stripping unit or means for feeding a major portion of carbon dioxide feed to said first stripping unit and means for feeding a remaining minor portion of carbon dioxide feed to said reactor for urea synthesis.

According to a further embodiment of the present invention, the second stripping unit is a thermal stripping unit with also carbon dioxide as stripping agent and the plant further comprises:

- means for feeding a (minor) portion of carbon dioxide feed to said second stripping unit.

In accordance with the present invention the plants for carrying out the urea production process may be either new or provided by modifying pre-existing plants. In the latter case, a production capacity expansion may be obtained and possibly a reduction of the energy consumption.

Further characteristics and advantages of the present invention are set forth in the detailed description of a preferred embodiment thereof given below by way of non-limiting example with reference to the annexed drawing.

BRIEF DESCRIPTION OF DRAWINGS

In such drawing.

MODES FOR CARRYING OUT THE INVENTION

Figure 1:
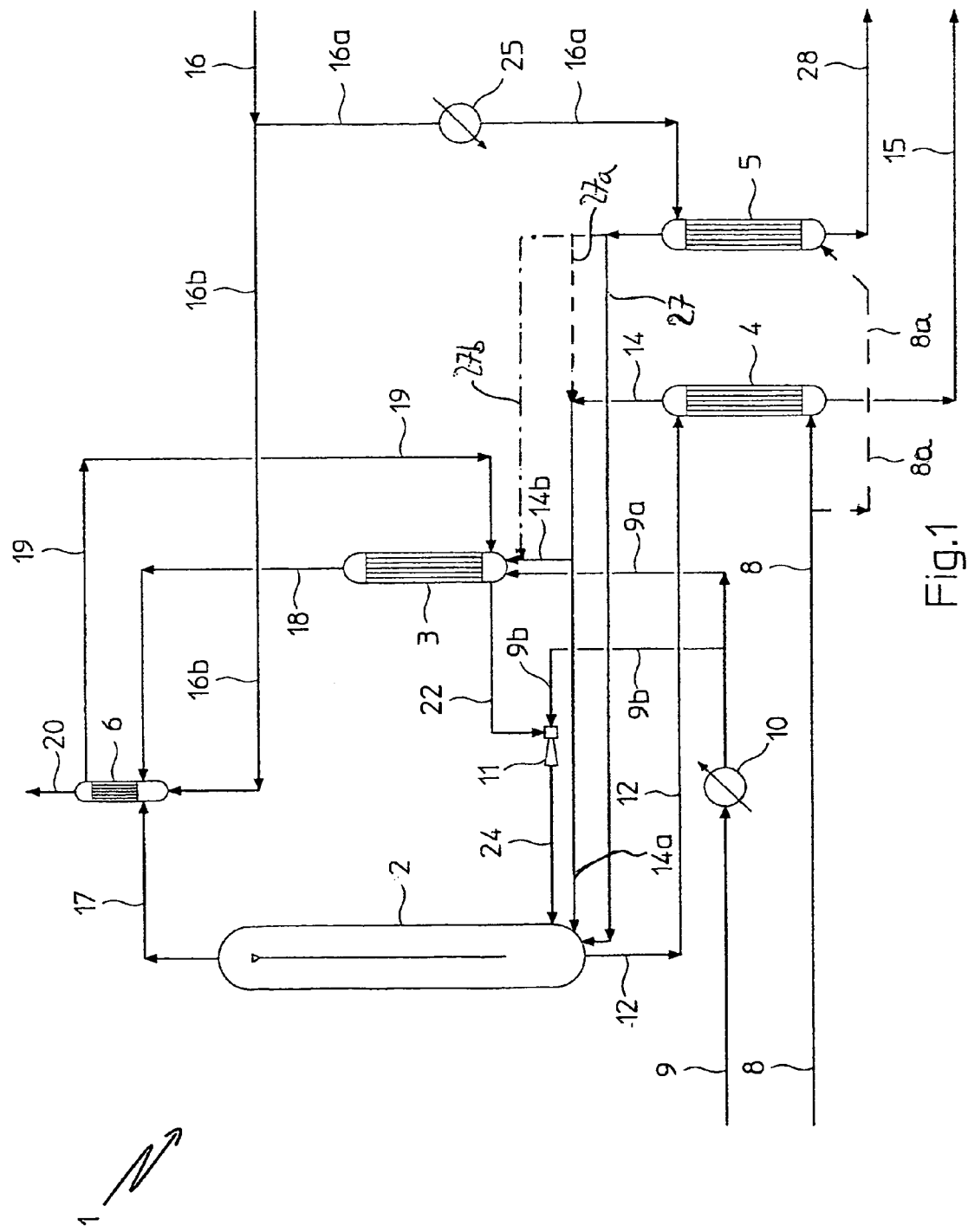
FIG. 1 illustrates schematically and partially a plant for urea production implementing the process according to the present invention.

Just to simplify the disclosure of the present invention, only a portion of a plant for urea production is schematically represented in the figure and more precisely the high pressure isobaric synthesis section (isobaric synthesis loop), the remaining sections (such as the urea recovery section) being not significant for the comprehension of the present invention have not been represented.

Further on, specific reference to the per se conventional connecting ducts of the various parts of. the plant described hereinbelow and illustrated in the figure as flow lines, will be made only when strictly necessary.

With reference to FIG. 1, a plant for urea production according to the invention is indicated with reference numeral 1.

Plant 1, and more specifically the high pressure synthesis section comprises a reactor or reaction space 2 for urea synthesis, a vertical condensation unit (condenser) 3 of the "submerged" type, a first stripping unit 4 with carbon dioxide for removing most of the unreacted carbamate and free ammonia of the reaction mixture coming from the reactor 2, and a second stripping unit 5.

Moreover, plant 1 comprises a washing unit 6, for removal of the passivating agents and other possible substances inert to the reaction, and a recovery section for the urea produced, which is not represented in FIG. 1.

The condenser 3, the first stripping unit 4 and the second stripping unit 5 generally operate at the same pressure conditions as the reactor 2.

The isobaric process pressure in the synthesis section of FIG. 1 is usually comprised between 140 and 160 bar.

The reactor 2 operates usually at a temperature comprised between 180° C. and 200° C., with a molar ratio $NH_3/CO_2$ comprised between 2.5 and 4, and a molar ratio $H_2O/CO_2$ lower than 0.5, preferably from 0.1 to 0.2.

The first and second stripping units 4 and 5 usually operate at a temperature comprised between 160 and 210° C. and the condenser 3 usually operate to at a temperature comprised between 150 and 210° C.

The synthesis section of plant 1 is disposed according to a so-called "vertical layout", where the reactor 2 and the condensation unit 3 are located at a higher level above the top of both the first stripping unit 4 and the second stripping unit 5.

Flow line 8 represents a gas flow comprising carbon dioxide feed, which is sent to the first stripping unit 4. It is contemplated to send a (minor) portion of the carbon dioxide feed to the second stripping unit 5 through the flow line 8a (shown in broken line in FIG. 1), if required by a specific situation.

Flow line 9 represents a liquid flow consisting essentially of ammonia feed. This gaseous flow is preheated in the exchanger 10 and split into two portions, one portion of which is sent to the condensation unit 3 through the flow line 9a and the other portion is sent to the ejector 11 through the flow line 9b and then to the reactor 2.

Flow line 12 represents a liquid flow of a reaction mixture coming from the reaction space 2 comprising urea, carbamate and free ammonia in aqueous solution.

This reaction mixture is fed into the stripping unit 4 where it is subjected to a treatment of partial decomposition of the carbamate and partial separation of said free ammonia in aqueous solution.

The stripping unit 4 operates with the carbon dioxide feed as stripping agent, which is fed to the stripping unit 4 through the flow line 8.

At the outlet of the stripping unit 4, flow lines 14 and 15 are shown which represent a first gas flow comprising ammonia and carbon dioxide in vapor phase and a liquid flow comprising urea and residual carbamate in aqueous solution, respectively.

The liquid flow 15 is fed to the urea recovery section (not shown) where the urea is separated at medium- and/or low-pressure, and a first flow of carbamate in aqueous solution is obtained. This solution, indicated by the flow line 16, is split into two portions, which are sent to the second stripping unit 5, through the flow line 16a, and to the washing unit 6 through the flow line 16b, respectively.

According to the present invention, the first gaseous flow 14 comprising ammonia and carbon dioxide in vapor phase is split into two portions, a first and a second portion, which are represented by flow lines 14a and 14b, respectively.

Particularly, the gaseous flow 14a (second portion) is sent directly to the reactor 2 to secure the reactor thermal balance, whereas the gaseous flow 14b (first portion) is sent to the condenser 3.

In the condenser 3, the ammonia and carbon dioxide in vapor phase of the gaseous flow 14b are brought into contact with a recycled flow comprising ammonia and carbamate in aqueous solution, coming from the washing unit 6 through flow line 19, and with the liquid flow 9a of the ammonia feed. These liquid flows 19 and 9a act as an absorption medium promoting the total condensation of said vapor phase.

Particularly, the above-mentioned recycled flow is obtained from the condensation, in the washing unit 6, of the ammonia and carbon dioxide in vapor phase coming from the reactor 2 through the flow line 17 and of the remaining gaseous phase that separates from the condensation unit 3, which is fed into the washing unit 6 through the flow line 18.

The above condensation is operated by means of a washing flow comprising a portion of the first flow of carbamate in aqueous solution coming from the urea recovery section, which is fed to the unit 6 through the flow line 16b.

The remaining gaseous phase that separates from condenser 3 though flow line 18, mainly contains inert substances and/or passivating agents together with possible uncondensed traces of ammonia and carbon dioxide in vapor phase.

In the washing unit 6, passivating agents and/or inert substances, generally introduced in the high pressure synthesis section through the carbon dioxide feed, are extracted from such section through flow line 20.

Instead, in the condensation unit 3, a substantially total condensation of the vapor phase 14b comprising ammonia and carbon dioxide takes place, so obtaining a liquid phase comprising carbamate in aqueous solution represented by the flow line 22 (i.e. a second flow of carbamate in aqueous solution).

This liquid flow 22 is sucked up by the ejector 11 which receive the portion 9b of the ammonia feed as driving fluid and is sent together with such a portion 9b to the reactor 2 through the flow line 24.

Moreover, the portion 16a of the first flow of carbamate in aqueous solution coming from the urea recovery section is preferably preheated in an heat exchanger 25 before advantageously entering the second stripping unit 5, Heat exchanger 25 preferably operates thanks to a part of the heat removed from the carbamate condenser 3.

According to the present invention, in the second stripping unit 5, main part of carbamate and free ammonia are removed from the carbamate solution as ammonia and carbon dioxide vapors with very low content of water (second flow comprising ammonia and carbon dioxide in vapor phase) and the vapor flow so obtained at the outlet of the second stripping unit 5, indicated by the flow line 27, is sent, according to a first embodiment, to the reactor 2, to complete the reactor thermal balance.

At the outlet of the second stripping unit 5, a flow of aqueous solution containing a residual content of carbamate and free ammonia, indicated by the flow line 28 (flow comprising residual carbamate in aqueous solution), is sent back to the urea recovery section for further processing.

According to a second embodiment of the invention, the urea plant comprises, instead of the flow line 27, a flow line 27a (shown in broken line in FIG. 1) connecting the second gas flow of ammonia and carbon dioxide in vapor phase with the first gas flow comprising ammonia and carbon dioxide in vapor phase (flow line 14). In other words, means (27a, 14b and 14a) are provided for recycling a first portion of said second flow comprising ammonia and carbon dioxide in vapor phase to said condensing means (condenser 3) and a second portion of said second flow comprising ammonia and carbon dioxide in vapor phase to said urea synthesis reactor 2.

According to a third embodiment of the invention, the second flow comprising ammonia and carbon dioxide in vapor phase obtained at the outlet of the second stripping unit 5 is sent, through flow lines 27b (shown in broken line in FIG. 1) and 14b, to the condensation unit 3 (flows 27a and 27 are missing).

Thanks to the present invention, the reactor thermal balance is totally secured by the gaseous flow 14a comprising ammonia and carbon dioxide coming from the first stripping unit 4 and possibly also by the gaseous flows 27 comprising ammonia and carbon dioxide coming from the second stripping unit 5.

This advantageously allows in principle to supply all carbon dioxide feed to the first stripping unit 4 improving the stripping efficiency of this unit and consequently reducing the investment, maintenance and operating costs of the plant, particularly of the stripping unit itself and of the urea recovery section. In this case, flow line 8a is missing However, a very high efficiency of the first stripping unit 4 can also be achieved supplying a major portion (at least 90%) of carbon dioxide feed to the first stripping unit 4 (flow line 8) and the remaining minor portion to the second stripping unit 5 (flow line 8a).

With a plant as described above, it is possible to carry out the process according to the present invention, wherein ammonia and carbon dioxide are made to react in the reactor 2, obtaining a reaction mixture comprising urea, carbamate and free ammonia in aqueous solution. The solution is fed to a first thermal stripping unit 4 with also carbon dioxide feed (flow line 8) as stripping agent and subjecting said mixture to a treatment of partial decomposition of carbamate and partial separation of free ammonia, obtaining a first flow comprising ammonia and carbon dioxide in vapor phase (flow line 14) and a flow comprising urea and residual carbamate in aqueous solution (flow line 15). The flow comprising urea and residual carbamate in aqueous solution is fed to a urea recovery section (flow line 15). In said recovery section the residual carbamate is separated from the urea to obtain a first flow of carbamate in aqueous solution (flow line 16). Advantageously, a first portion of said first flow comprising ammonia and carbon dioxide in vapor phase is recycled through recycling means 14b in condensation unit 3 and subjected to a substantially total condensation to obtain a second flow of carbamate in aqueous solution. Said second flow of carbamate in aqueous solution is then recycled through recycling means 22 to the reaction space 2. A second portion of said first flow comprising ammonia and carbon dioxide in vapor phase is directly recycled through recycling means 14a to the reaction space 2. Furthermore, at least part of the first flow of carbamate in aqueous solution obtained in said urea recovery section is recycled through recycling means 16a to a second stripper unit 5 and subjected to a treatment of partial decomposition to obtain a second flow comprising ammonia and carbon dioxide in vapor phase and a flow comprising residual carbamate in aqueous solution.

According to a first embodiment of the present invention, said second flow comprising ammonia and carbon dioxide in vapor phase is recycled to said reaction space 2 through recycling means 27.

According to a further embodiment, said second flow comprising ammonia and carbon dioxide in vapor phase is recycled to said first portion of said first flow comprising ammonia and carbon dioxide in vapor phase through recycling means 27b and then recycled together with the first portion to the condensation unit 3 where they are subjected to a substantially total condensation to obtain said second flow of carbamate in aqueous solution.

According to still another embodiment, said second flow comprising ammonia and carbon dioxide. In vapor phase is recycled through recycling means 27a to said first flow comprising ammonia and carbon dioxide in vapor phase, a first portion thereof is recycled through recycling means 14b to said condensation unit 3 and subjected to substantially total condensation to obtain said second flow of carbamate in aqueous solution, a second portion thereof is instead recycled to said reaction space 2 trough recycling means 14a.

Preferably, with the plant shown in FIG. 1 it is also possible to carry out a process wherein the liquid ammonia feed is fed in a first portion directly in said reactor 2 for urea synthesis through recycling means 9b and in a second portion to the condensation unit 3 through recycle means 9a.

Moreover, the present plant also allows to carrying out a process having the steps of:
preheating said at least part of the first flow of carbamate in aqueous solution to be sent to the second stripping unit, and
preheating said first portion of liquid ammonia feed to be sent to the urea synthesis reactor and/or said second portion of liquid ammonia feed to be sent to the condensation unit.

Advantageously, the above preheating steps are achieved using the heat removed in the condensing means to secure minimum energy consumption.

The so conceived invention is subjected to variations and changes, all falling within the scope of protection defined by the following claims.

For example, it is possible to provide for two separate condensation units (not shown) for substantially totally condensing the first and the second flow comprising ammonia and carbon dioxide in vapor phase, respectively.

The invention claimed is:

1. Process for urea production of the type comprising the steps of:

performing a reaction between ammonia and carbon dioxide in a reaction space to obtain a reaction mixture comprising urea, carbamate and free ammonia in aqueous solution, subjecting said mixture to a stripping treatment with carbon dioxide feed as a stripping agent to obtain a first flow comprising ammonia and carbon dioxide in vapor phase and a flow comprising urea and residual carbamate in aqueous solution, feeding said flow comprising urea and residual carbamate in aqueous solution to a urea recovery section, separating in said recovery section said residual carbamate from the urea to obtain a first flow of carbamate in aqueous solution, characterized in that it comprises the additional steps of:

subjecting a first portion of said first flow comprising ammonia and carbon dioxide in vapor phase to a substantially total condensation to obtain a second flow of carbamate in aqueous solution, recycling said second flow of carbamate in aqueous solution to said reaction space, recycling a second portion of said first flow comprising ammonia and carbon dioxide in vapor phase to said reaction space, subjecting at least part of said first flow of carbamate in aqueous solution obtained in said urea recovery section to a treatment of partial decomposition to obtain a second flow comprising ammonia and carbon dioxide in vapor phase and a flow comprising residual carbamate in aqueous solution, recycling said second flow comprising ammonia and carbon dioxide in vapor phase to said reaction space, or recycling said second flow comprising ammonia and carbon dioxide in vapor phase to said first portion of said first flow comprising ammonia and carbon dioxide in vapor phase and subjecting them to a substantially total condensation to obtain said second flow of carbamate in aqueous solution, or recycling said second flow comprising ammonia and carbon dioxide in vapor phase to said first flow comprising ammonia and carbon dioxide in vapor phase and subjecting a first portion thereof to a substantially total condensation to obtain said second flow of carbamate in aqueous solution and recycling a second portion thereof to said reaction space.

2. Process according to claim 1, characterized in that the treatment of partial decomposition of the said at least part of the first flow of carbamate in aqueous solution is carried out at a pressure substantially corresponding to the pressure in the reaction space.

3. Process according to claim 1, characterized in that it further comprises the step of feeding the flow comprising residual carbamate in aqueous solution resulting from the treatment of partial decomposition of at least part of the first flow of carbamate in aqueous solution to said urea recovery section.

4. Plant (1) for urea production comprising:

a urea synthesis reactor (2) for performing a reaction between ammonia and carbon dioxide obtaining a reaction mixture comprising urea, carbamate and free ammonia in aqueous solution, a first thermal stripping unit (4) with also carbon dioxide as stripping agent for subjecting said reaction mixture to a treatment of partial decomposition of the carbamate and partial separation of the free ammonia in aqueous solution present in said mixture obtaining a first flow comprising ammonia and carbon dioxide in vapor phase and a flow comprising urea and residual carbamate in aqueous solution, a urea recovery section for separating urea from said flow comprising urea and residual carbamate in aqueous solution leaving the first stripping unit, obtaining a first flow of carbamate in aqueous solution, which is characterized in that it further comprises:

means (3) for substantially totally condensing a first portion of said first flow comprising ammonia and carbon dioxide in vapor phase obtaining a second flow of carbamate in aqueous solution, means (22, 24) for recycling said second flow of carbamate in aqueous solution to said urea synthesis reactor (2), means (14, 14b) for recycling a second portion of said first flow comprising ammonia and carbon dioxide in vapor phase to said urea synthesis reactor (2), a second stripping unit (5) for subjecting at least part of said first flow of carbamate in aqueous solution to a treatment of partial decomposition obtaining a second flow comprising ammonia and carbon dioxide in vapor phase, means (27) for recycling said second flow comprising ammonia and carbon dioxide in vapor phase to said urea synthesis reactor (2), or means (27b) for recycling said second flow comprising ammonia and carbon dioxide in vapor phase to said condensing means (3), or means (27a) for recycling a first portion of said second flow comprising ammonia and carbon dioxide in vapor phase to said condensing means (3) and a second portion of said second flow comprising ammonia and carbon dioxide in vapor phase to said urea synthesis reactor (2).

5. Plant according to claim 4, characterized in that said means (3) for totally condensing said first portion of the first flow comprising ammonia and carbon dioxide in vapor phase comprises a vertical carbamate condensation unit (3) of the submerged type.

6. Plant according to claim 5, characterized in that it further comprises:

means (9,9b, 11,24) for feeding a first portion of liquid ammonia feed in said reactor (2) for urea synthesis, and means (9,9a) for feeding a second portion of liquid ammonia feed to said condensing means (3).

7. Plant according to claim 5, characterized in that it further comprises:

means (25) for preheating said at least part of the first flow of carbamate solution to be sent to the second stripping unit (5), and means (10) for preheating said first portion of liquid ammonia feed to be sent to the urea synthesis reactor (2) and/or said second portion of liquid ammonia feed to be sent to the condensing means (3).

8. Plant according to claim 6, characterized in that said means (9,9b,11,24) for feeding the first portion of liquid ammonia feed to said reactor (2) and said means (11,22,24) for recycling the second flow of carbamate in aqueous solution to said reactor (2) comprise:
- an ejector (11),
- means (22) for feeding said second flow of carbamate in aqueous solution to the ejector (11),
- means (9,9b) for feeding said first portion of liquid ammonia feed to the ejector (11), and
- means (24) for sending said second flow of carbamate in aqueous solution together with said first portion of liquid ammonia feed from the ejector (11) to the urea synthesis reactor (2).

9. A plant according to claim 4, characterized in that said second stripping unit (5) is a thermal stripping unit with also carbon dioxide as stripping agent and in that it further comprises:
- means (8) for feeding a major portion of said carbon dioxide feed to said first stripping unit (4), and
- means (8a) for feeding a remaining minor portion of said carbon dioxide feed to said second stripping unit (5).

* * * * *